(12) United States Patent
Wu et al.

(10) Patent No.: US 7,929,659 B2
(45) Date of Patent: Apr. 19, 2011

(54) SYSTEM AND METHOD FOR GENERATING COMPUTED TOMOGRAPHY IMAGES

(75) Inventors: Xiaoye Wu, Rexford, NY (US); Fang Frank Dong, New Berlin, WI (US); James Walter Leblanc, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 461 days.

(21) Appl. No.: 12/179,298

(22) Filed: Jul. 24, 2008

(65) Prior Publication Data

US 2010/0020921 A1 Jan. 28, 2010

(51) Int. Cl.
*A61B 6/03* (2006.01)
(52) U.S. Cl. .......... 378/4; 378/9; 378/19; 378/901
(58) Field of Classification Search ........ 378/4, 9, 378/19, 901; 382/128–131
See application file for complete search history.

(56) References Cited

U.S. PATENT DOCUMENTS

| | | |
|---|---|---|
| 4,670,840 A | 6/1987 | Freundlich |
| 5,173,852 A | 12/1992 | Lonn |
| 5,265,142 A | 11/1993 | Hsieh |
| 5,361,291 A | 11/1994 | Toth et al. |
| 5,533,081 A | 7/1996 | Hsieh |
| 5,745,542 A | 4/1998 | Gordon et al. |
| 5,841,829 A | 11/1998 | Dolazza et al. |
| 6,115,445 A | 9/2000 | Lai |
| 2006/0056579 A1 | 3/2006 | Stierstorfer |
| 2008/0019607 A1 | 1/2008 | Star-Lack et al. |

FOREIGN PATENT DOCUMENTS

| | | | |
|---|---|---|---|
| JP | 2006239049 A | * | 9/2006 |
| WO | WO 2005072612 A1 | | 8/2005 |

\* cited by examiner

*Primary Examiner* — Edward J Glick
*Assistant Examiner* — John M Corbett
(74) *Attorney, Agent, or Firm* — Fletcher Yoder

(57) ABSTRACT

A computed tomographic imaging system is provided for generating computed tomography images. The computed tomographic system includes a processor configured to access image data encoding X-ray projections at a detector position and a plurality of X-ray source beam focal spot positions and to align pixel values for the projections in a direction of deviation of the positions. The processor is also configured to determine a correction factor for at least one of the projections based upon the aligned pixel values and upon a sum of the projections and to correct the pixel values for the at least one of the projections based upon the correction factor.

23 Claims, 6 Drawing Sheets

SYSTEM AND METHOD FOR GENERATING COMPUTED TOMOGRAPHY IMAGES

BACKGROUND

The invention relates generally to computed tomography (CT) imaging and more particularly, to a technique for reducing ring artifacts and image noise in images acquired via a computed tomography systems using focal spot wobble.

In a current computed tomography system, an X-ray source projects a fan-shaped or cone-shaped beam which is collimated to lie within an X-Y plane of a Cartesian coordinate system, termed the "imaging plane." The X-ray beam passes through an object being imaged, such as a medical patient, and impinges upon an array of radiation detectors. The detector array includes detector elements, centered on a "pitch, each of which measure the intensity of transmitted radiation along a beam projected from the X-ray source to the particular detector element. The intensity of the transmitted radiation is dependent upon the attenuation of the X-ray beam by the object and each detector produces a separate electrical signal that is a measurement of the beam attenuation. The signals are processed and reconstructed to form images which may be evaluated themselves or which may be associated to form a volume rendering or other representation of the imaged region. In a medical context, pathologies or other structures of interest may then be located or identified from the reconstructed or rendered volume.

The source and detector array in a conventional "third generation" CT system are rotated on a gantry around the object so that the angle at which the X-ray beam intersects the object changes during data acquisition. A group of X-ray attenuation measurements from the detector array at a given angle is referred to as a "view" and a "scan" of the object comprises a set of views made at different angular orientations during one revolution of the X-ray source and detector. These projections are collected to form a tomographic projection set.

The acquired tomographic projection sets are typically stored in numerical form for computer processing to "reconstruct" a slice image according to reconstruction algorithms known in the art. For example, a projection set of fan beam projections may be reconstructed directly into an image by means of fan beam reconstruction techniques, or the intensity data of the projections may be sorted into parallel beams and reconstructed according to parallel beam reconstruction techniques. The reconstructed tomographic images may be displayed on a conventional display, such as a CRT, LCD, or plasma display.

To improve spatial resolution of an X-ray CT system, the X-ray focal spot may be rapidly moved back and forward between a number of pre-determined positions during scanning. This process is commonly referred to as focal spot wobble. By interleaving the projection data from these wobbled focal spots, new projections can be obtained with higher sampling frequency, resulting in better image resolution. However, in some circumstances, consistent mis-match between the projections may create a ring artifact in the image while random mis-match may increase image noise. Such mis-matches may be present due to factors such as inaccurate air normalization, unstable X-ray focal points, patient motion, detector spectral response variation at different focal points and so forth. These errors normally are present in a non-wobble CT system as well, but due to the fact that such errors alter the entire projection smoothly, and the fact that the application of a high pass filter is done in the reconstruction process, these near constant errors are greatly suppressed in non-wobble systems. But, in a focal spot wobbling system, interleaving the near constant errors can result in high frequency errors.

It is therefore desirable to remove these high frequency errors and the resulting ring artifacts and image noise that may be present in focal spot wobbling systems without impacting the spatial resolution of such systems.

BRIEF DESCRIPTION

Briefly in accordance with one aspect of the technique, a method is provided for producing a computed tomography image. The method provides for accessing image data encoding X-ray projections at a detector position and a plurality of X-ray source beam focal spot positions, aligning pixel values for the projections in a direction of deviation of the positions, determining a correction factor for at least one of the projections based upon the aligned pixel values and upon a sum of the projections, and correcting the pixel values for the at least one of the projections using the correction factor. Systems and computer programs that afford functionality of the type defined by this method may also be provided by the present technique.

In accordance with another aspect of the technique, a method is provided for producing a computed tomography image. The method provides for accessing image data encoding X-ray projection at a detector position and a plurality of X-ray source beam focal spot positions. The source beam focal spot positions are obtained by impacting a target within the X-ray source by an electron beam steered differently at the target for each focal spot position. The method also provides for aligning pixel values for the projections in a direction of deviation of the positions, grouping the pixel values into a plurality of sub-regions, for each sub-region, based upon the aligned pixel values, determining a respective correction factor for at least one of the projections based upon a sum of the projections and a number of pixels in the sub-region, and correcting the pixel values for the at least one of the projections based upon the respective correction factor for each sub-region. Moreover, the method provides for repeating the determining and correcting steps for each projection to be corrected and for each sub-region. Here again, systems and computer programs affording such functionality may be provided by the present technique.

In accordance with a further aspect of the present technique a computed tomographic imaging system is provided. The computed tomographic system includes a processor configured to access image data encoding X-ray projections at a detector position and a plurality of X-ray source beam focal spot positions, to align pixel values for the projections in a direction of deviation of the positions, to determine a correction factor for at least one of the projections based upon the aligned pixel values and upon a sum of the projections, and to correct the pixel values for the at least one of the projections based upon the correction factor.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present techniques are generally directed to the reconstruction of images acquired via CT systems using focal spot wobble so as to minimize ring artifacts and noises. Though the present discussion provides examples in context of medical imaging systems, one of ordinary skill in the art will readily comprehend that the application of these techniques in other contexts, such as for industrial imaging, security screening, and or baggage or package inspection, is well within the scope of the present techniques.

Figure 1:
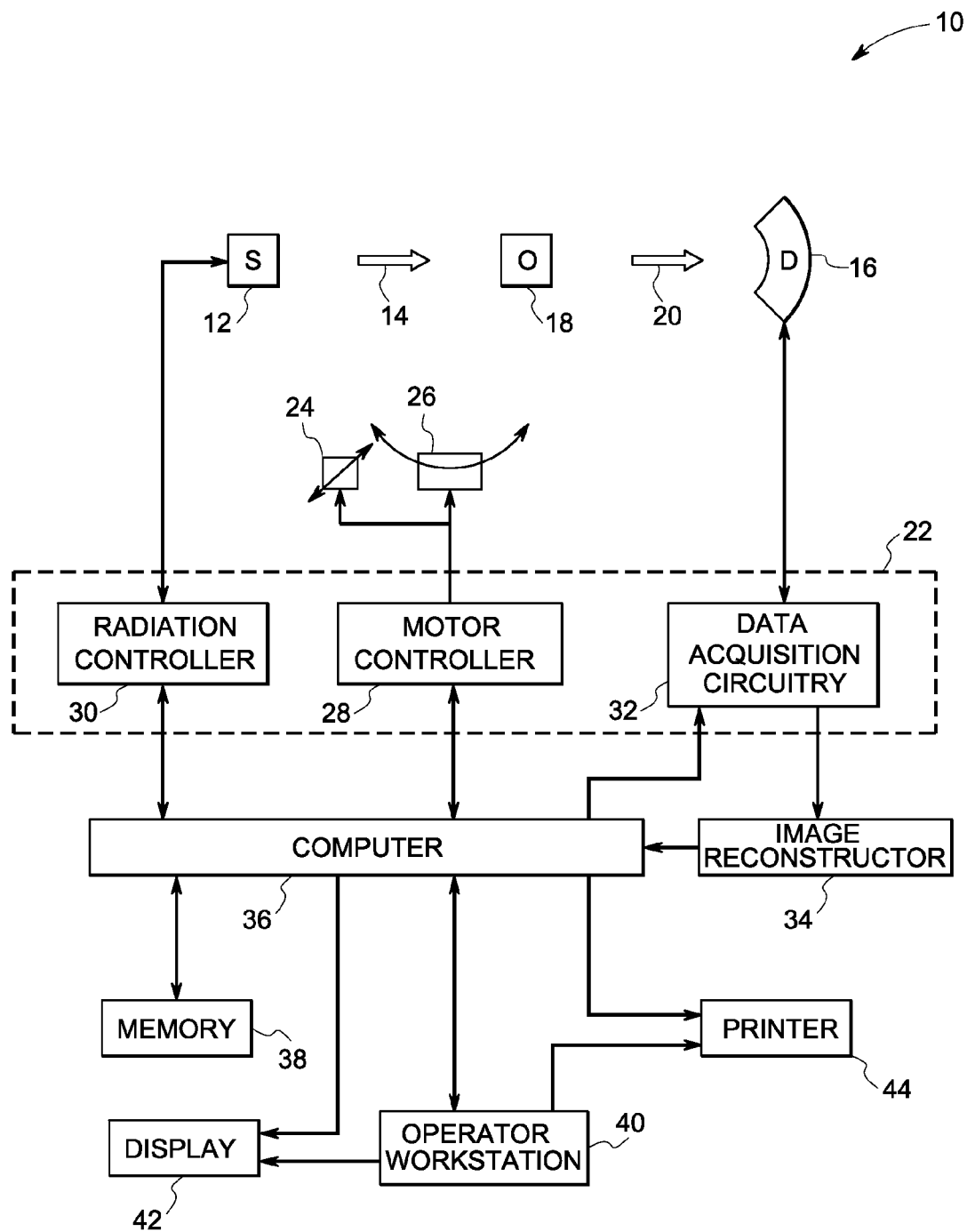
FIG. 1 is a schematic diagram of a CT system in accordance with the aspects of the present technique.

Referring now to FIG. 1, an imaging system 10 for use in accordance with the present technique is illustrated. The imaging system 10 is adapted to acquire projection images and to process the acquired projection images before reconstruction in accordance with aspects of the present technique. In the illustrated embodiment, the imaging system 10 includes a radiation source 12, such as an X-ray source. A collimator may be positioned adjacent to the radiation source 12 for regulating the size and the shape of a stream of radiation 14 that emerges from the radiation source 12.

In typical operation, the radiation source 12 projects a stream of radiation 14 towards a detector array 16 placed on the opposite side of the radiation source 12. The stream of radiation 14 passes into an imaging volume in which an object 18 to be imaged may be positioned. The object 18 may be a subject of interest such as a human patient, or, in other contexts, a part, package, or piece of luggage to be screened. It should be noted that a particular region of the object 18 may be chosen by an operator for imaging so that the most useful scan of the region may be acquired.

An attenuated portion of the radiation 20 passes through or around the object 18, which provides the attenuation, and impacts the detector array 16. It should be noted that portions of the radiation 14 may extend beyond the boundary of the object 18 and may also impact detector 16 without being attenuated by the object 18. The detector array 16 may be a single slice detector or a multi-slice detector and is generally formed as an array of detection elements. Each detector element, when impacted by the radiation 20, produces an electrical signal that represents the intensity of the incident radiation 20 at the position of the detector element. These signals are acquired and processed to reconstruct an image of the features internal as well external to the object 18.

The object 18 and the radiation source 12 may be displaced relative to each other, allowing projection data to be acquired at various views relative to the object 18 if desired. For example, the object 18 may be positioned on a table, such as a turntable, so that the object 18 may be rotated during the examination process to expose all sides of the object 18 to the stream of radiation 14. Alternatively, the radiation source 12 and/or the detector array 16 may be disposed on a gantry, which may be rotated around the object 18 during the examination process. As the object 18 and the radiation source 12 rotate relative to each other, the detector array 16 collects data of radiation attenuation at the various view angles relative to the object 18. Thus, an image or slice is acquired which may incorporate, in certain modes, less or more than 360 degrees of projection data, to formulate an image.

Operation of the source 12 is controlled by a system controller 22, which furnishes both power, and control signals for examination sequences. Moreover, the detector array 16 is coupled to the system controller 22, which commands acquisition of the signals generated in the detector array 16. The system controller 22 may also execute various signal processing and filtration functions, such as for initial adjustment of dynamic ranges, interleaving of digital image data, and so forth. In general, system controller 22 commands operation of the imaging system 10 to execute examination protocols and to process acquired data. In the present context, system controller 22 may also include signal processing circuitry and other circuitry, typically based upon a general purpose or application-specific digital computer, associated memory circuitry for storing programs and routines executed by the computer, as well as configuration parameters and image data, interface circuits, and so forth. For example, the associated memory circuitry may store programs or codes for implementing the present technique. Indeed, the system controller 22 may be implemented as hardware and/or software components of the depicted computer 36.

In the embodiment illustrated in FIG. 1, the system controller 22 is coupled to a linear positioning subsystem 24 and a rotational subsystem 26. In particular, the system controller 22 may include a motor controller 28 that controls the operation of the linear positioning subsystem 24 and the rotational subsystem 26. The rotational subsystem 26 enables the X-ray source assembly and/or the detector assembly to be rotated one or multiple turns around the object 18. It should be noted that the rotational subsystem 26 might include a gantry. Thus, the system controller 22 may be utilized to control the rotational speed and position of the gantry. Alternatively, the rotational subsystem 26 may include a motorized turntable and the system controller 22 may be configured to rotate the motorized turntable, thereby rotating the object 18 one or multiple turns during an examination. The linear positioning subsystem 24 enables the object 18 to be displaced linearly, such as by moving a table or support on which the object 18 rests. Thus, in one embodiment, the table may be linearly moved within a gantry to generate images of particular areas of the object 18.

Additionally, as will be appreciated by those skilled in the art, the radiation source 12 may be controlled by a radiation controller 30 provided as part of the system controller 22. Particularly, the radiation controller 30 may be configured to provide power and timing signals to the radiation source 12. Further, the system controller 22 may include data acquisition circuitry 32. In this exemplary embodiment, the detector array 16 is coupled to the system controller 22, and more particularly to the data acquisition circuitry 32. The data acquisition circuitry 32 receives data collected by readout electronics of the detector array 16. The data acquisition circuitry 32 typically receives sampled analog signals from the detector array 16 and converts the data to digital signals for subsequent processing and reconstruction by an image reconstructor 34 and/or a computer 36.

The computer 36 is typically coupled to the system controller 22. The image reconstructor 34 may be coupled to or may be a part of a computer 36. The sampled and digitized data collected by the data acquisition circuitry 32 may be transmitted to the image reconstructor 34 and/or the computer 36 for subsequent processing and reconstruction. For example, the data collected from the detector array 16 may undergo pre-processing and calibration at the data acquisition circuitry 32, the image reconstructor 34, and/or the computer 36 to condition the data to represent the line integrals of the attenuation coefficients of the scanned objects. The processed data, commonly called projections, may then be reordered, filtered, and backprojected to formulate an image of the scanned area, as discussed in greater detail below. As will be appreciated by those skilled in the art, although the present techniques may be used with projection X-ray systems, when used with CT or tomosynthesis systems, in addition to typical filtered back-projection reconstruction algorithms, any suitable reconstruction algorithm may be employed, including statistical reconstruction approaches. Once reconstructed, the image produced by the imaging system 10 reveals internal as well as external features of the object 18 which may be used for diagnosis, evaluation, and so forth.

The computer 36 may include or be in communication with a memory 38 that can store data processed by the computer 36 or data to be processed by the computer 36. It should be understood that any type of computer accessible memory device capable of storing the desired amount of data and/or code may be utilized by such an exemplary imaging system 10. Moreover, the memory 38 may comprise one or more memory devices, such as magnetic, solid state, or optical devices, of similar or different types, which may be local and/or remote to the system 10. The memory 38 may store data, processing parameters, and/or computer programs comprising one or more routines for performing the processes described herein. Furthermore, memory 38 may be coupled directly to system controller 22 to facilitate the storage of acquired data.

The computer 36 may also be adapted to control features enabled by the system controller 22, i.e., scanning operations and data acquisition. Furthermore, the computer 36 may be configured to receive commands and scanning parameters from an operator via an operator workstation 40. For example, the operator workstation 40 may be equipped with a keyboard and/or other input devices by which an operator may control the imaging system 10. Thus, the operator may observe the reconstructed image and other data relevant to the system from computer 36, initiate imaging, select a spectrum for imaging and so forth.

A display 42 may be coupled to the operator workstation 40 and/or the computer 36 and may be utilized to observe the reconstructed image and/or to control imaging. Additionally, the scanned image may also be printed by a printer 44 which may be coupled to the computer 36 and/or the operator workstation 40, either directly or over a network. Further, the operator workstation 40 and/or the computer 36 may be coupled to a picture archiving and communications system (PACS). In such an embodiment, the PACS might be coupled to a remote system, such as a radiology department information system (RIS), hospital information system (HIS) or to an internal or external network, so that others at different locations may gain access to the image data. It should be further noted that the computer 36 and/or operator workstation 40 may be coupled to other output devices that may include standard or special purpose computer monitors and associated processing circuitry. Furthermore, additional operator workstations may be further linked in the imaging system 10 for outputting system parameters, requesting inspection, viewing images, and so forth, so that more than one operator may perform operations related to the imaging system 10. For example, one operator may utilize one operator workstation to image acquisition while a second operator utilizes a second operator workstation to reconstruct and/or review the results of the imaging routines. In general, displays, printers, workstations, and similar devices supplied within the imaging system 10 may be local to the data acquisition components, or may be remote from these components linked to the imaging system 10 via one or more configurable networks, such as the Internet, virtual private networks, and so forth.

Figure 2:
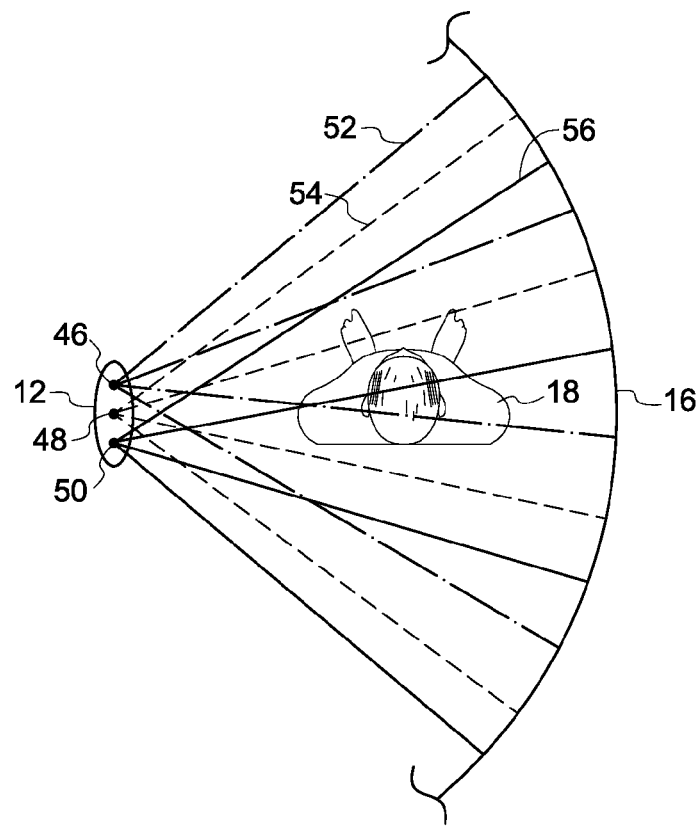
FIG. 2 illustrates X-ray beams emitted via an X-ray source having a focal spot wobble in accordance with the aspects of the present technique.

A wide variety of technique may be employed to acquire projection images of the object and to reconstruct the acquired projection images for diagnostic and/or evaluation purposes. For example, the exemplary imaging system 10 may be adapted to acquire sets of projection images of the imaged object and/or to generate a reconstructed image based on acquired projection images for detailed evaluation or examination. Referring now to FIG. 2, the X-ray source 12 employed by the imaging system 10 described above may be provided with focal spot wobble capability (also known as flying focal spot capability) so as to improve the spatial resolution of the imaging system 10. In such an embodiment, the X-ray focal spot may be rapidly moved backward and forward between a number of predetermined positions during scanning. This is referred to as focal spot wobbling. In one embodiment, the movement of the focal spot may be in the direction of the x-y plane of the Cartesian co-ordinate system where the X-ray beam is oriented to lie, this is termed as the "imaging plane". In another embodiment the movement of the focal spot may be in the direction perpendicular to the imaging plane to improve the out-of-imaging plane resolution. By interleaving the projection data from these wobbled focal spots, new projections can be obtained with higher sampling frequency, resulting in better image resolution. To interleave the projections from a number of wobbled focal points to make a single projection with increased sampling frequency, it may be useful if the projections from the wobbled focal points match seamlessly without differential errors or DC errors between them.

For example, as illustrated in FIG. 2, the X-ray source 12 is wobbled at three focal spot positions 46, 48 and 50. In one embodiment, the X-ray source beam focal spot positions may be obtained by impacting a target within an X-ray source 12 by an electron beam steered differently at the target for each focal spot position. For example, in the depicted embodiment, the first focal spot position 46 is where the beam of X-ray 52 is generated by impacting a first location on a target with a steered electron beam. Similarly, the second focal spot position 48 is where the beam of X-ray 54 is generated at a second location on the target and the third focal spot position 50 is where the beam of X-ray 56 is generated at a third location on the target. According to an embodiment of the present technique, the X-ray source beam focal spot positions may be deviated in a direction transverse to an imaging plane. In other embodiments, however, the X-ray source beam focal spot positions may be deviated in a direction parallel to or within the imaging plane. The beams so generated may pass through or around the object 18, such as a patient, and impact the detector array 16. The detected radiation may be processed to form projection images as discussed above.

Figure 3:
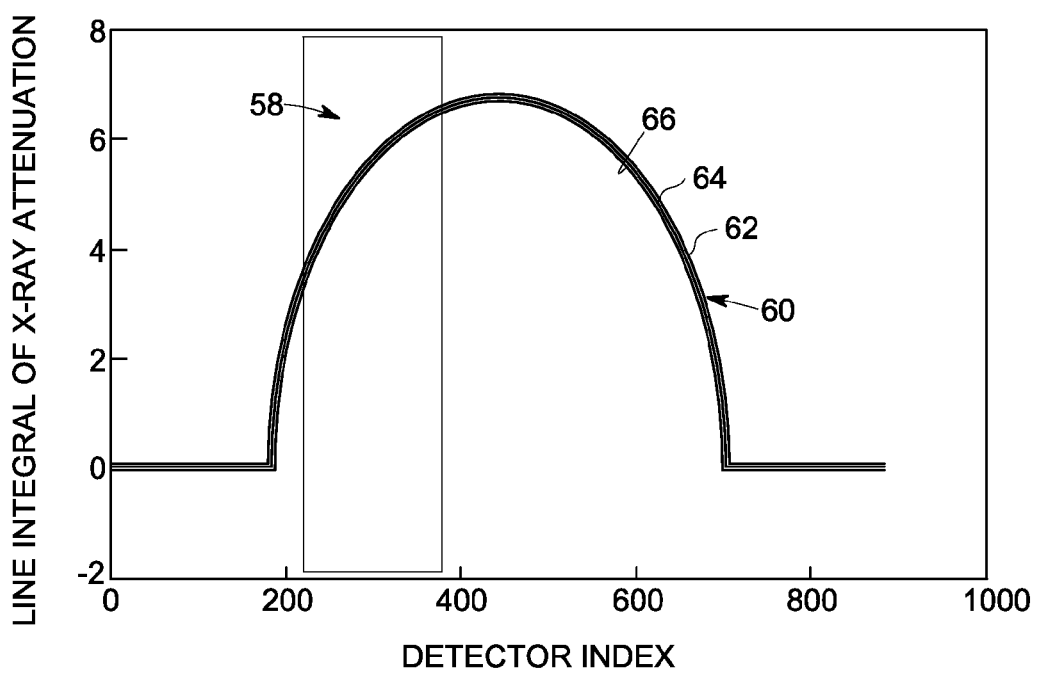
FIG. 3 depicts a projection profile of an image of a phantom in accordance with the aspects of the present technique.

A projection profile of an image of a phantom acquired by the imaging system 10 using focal spot wobble is illustrated in FIG. 3 where the horizontal axis of the graph represents the detector index and the vertical axis represents line integral of X-ray attenuation. As illustrated, the projection profile 60 includes three projection profiles each generated via streams of radiation emitted from respective three focal spot positions. The first profile 62 is obtained from the focal spot position 46 while the second projection profile 64 and the third projection profile 66 are obtained from the respective second and third focal spot position 48 and 50.

Figure 4:
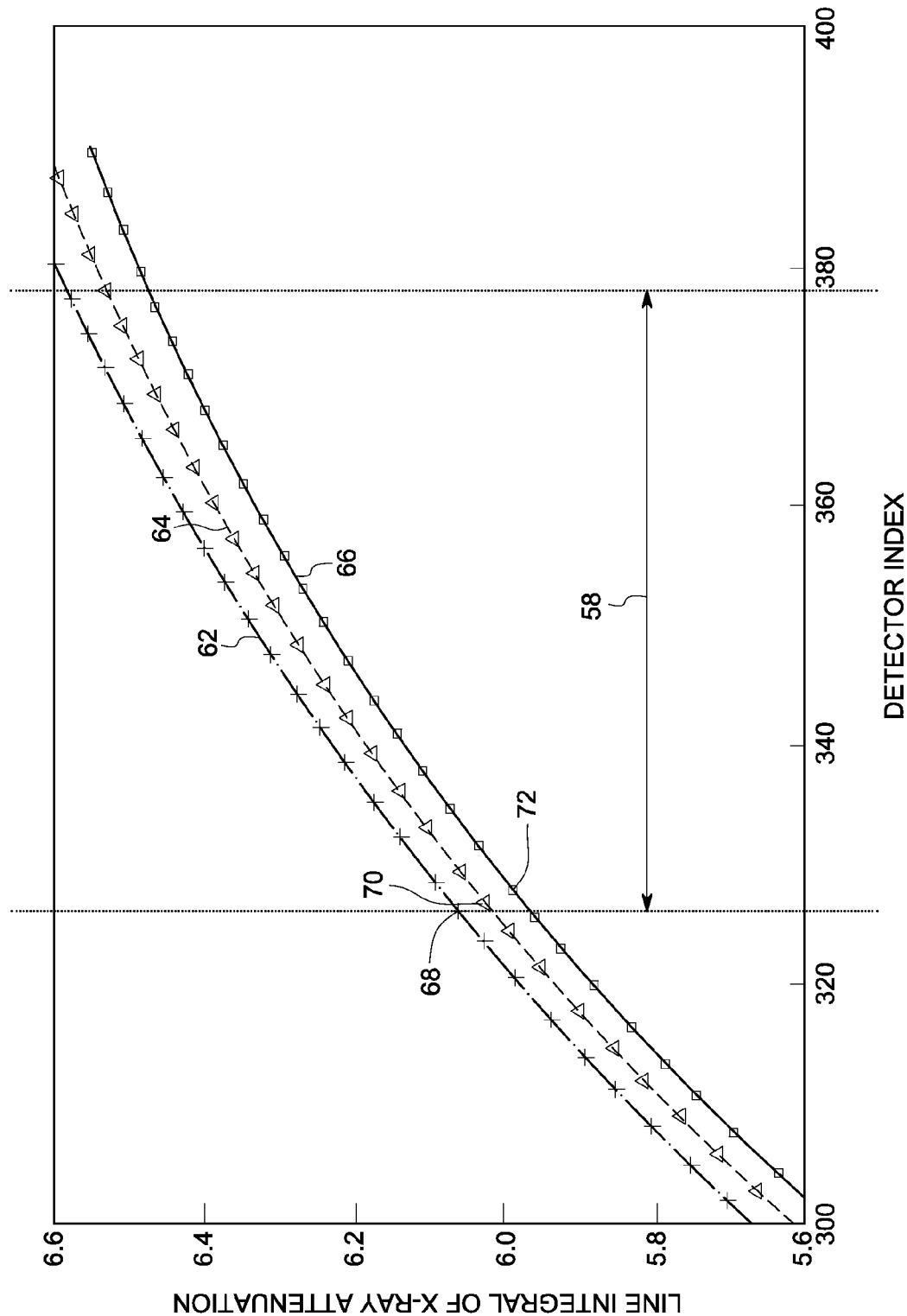
FIG. 4 depicts a sub-region of the projection profile of the image of a phantom shown in FIG. 3 in accordance with the aspects of the present technique.

An exploded view of a sub-region 58 of the projection profile 60 of FIG. 3 is illustrated in FIG. 4. A reference position 68 of the projection profile 62 for an actual position in the phantom from the first focal spot position is shown. The same position in the phantom is given by the reference position 70 in the projection profile 64 and by the reference position 72 in the projection profile 66. It should be noted that, the reference position of the image is the pixel value for the projections. As illustrated, the reference positions 68, 70 and 72 are misaligned (i.e., the pixel values for the projections are not aligned). According to an embodiment, the physical distance between the reference positions 68 and 70 and, between reference positions 70 and 72 of the image are approximately one third of the detector pixel pitch for a three focal spot wobble position X-ray CT system. It is this misalignment in the pixel position that leads to ring artifacts in the reconstructed images. Thus, to reduce or minimize the ring artifacts in the images, the misalignment may be corrected in accordance with aspects of the present technique. In one embodiment, this may be achieved by aligning pixel values for the projections in a direction of deviation of the positions, determining a correction factor for at least one of the projections based upon the aligned pixel values and upon a sum of the projections, and correcting the pixel values for the at least one of the projections using the correction factor.

Figure 5:
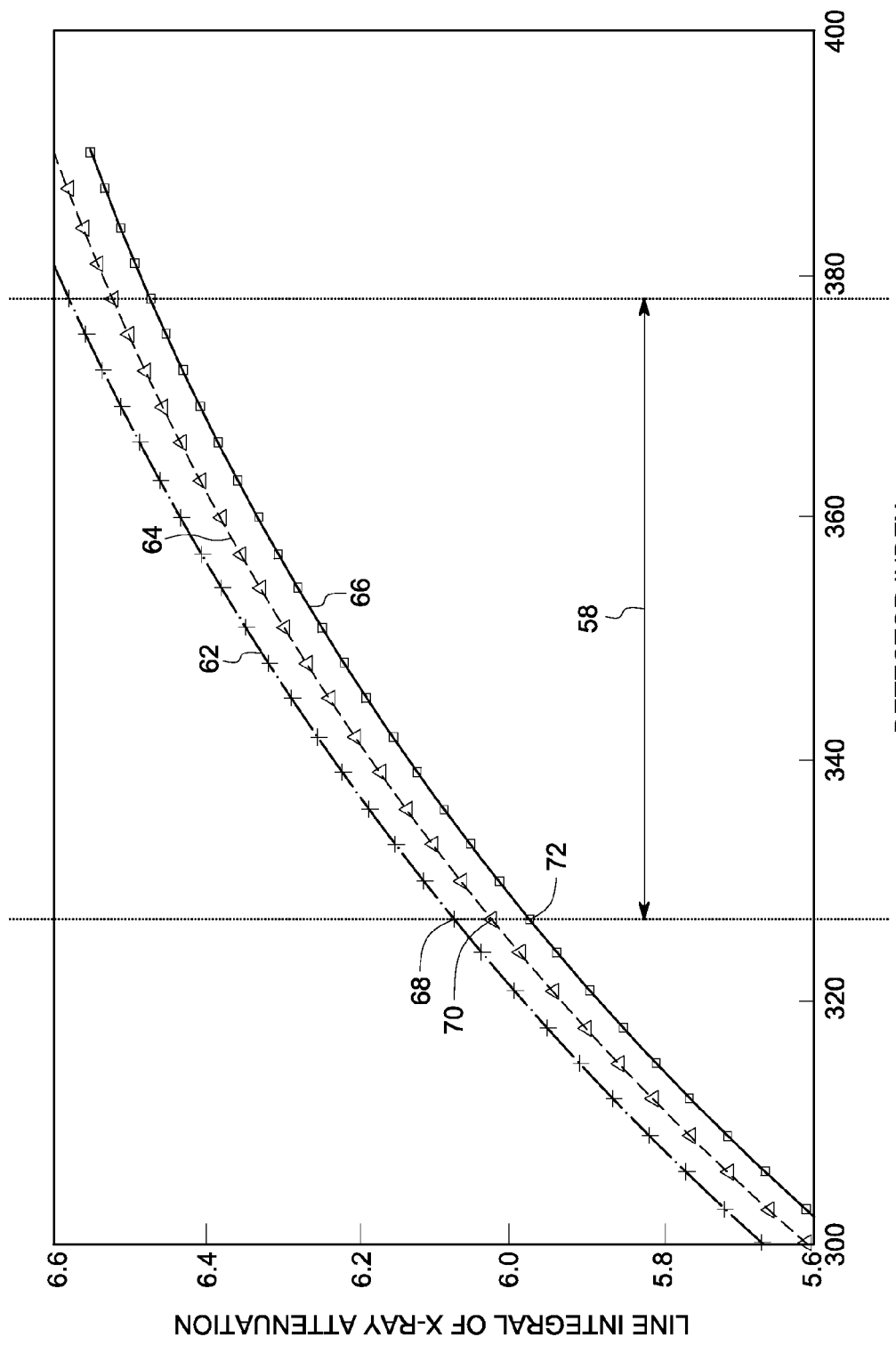
FIG. 5 depicts the sub-region of the projection profile of the image of a phantom after sampling in accordance with the aspects of the present technique.

For example, FIG. 5 illustrates the three reference positions 68, 70 and 72 after sampling in accordance with aspects of the present technique. The X-ray projection 62 from first focal spot position is taken as a reference and the pixel values for the other projections 64 and 66, are aligned along the x-direction. In the depicted implementation, the reference position 70 on X-ray projection 64 and the reference position 72 on X-ray projection 66 are aligned with respect to the reference position 68 on X-ray projection 62. In one embodiment this may be done by resampling by linear weighting, non-linear weighting and other known techniques. In one embodiment, the pixel values for the projection 62 which is used as a reference are not corrected. Thus, in certain embodiments, one of the X-ray projections may be taken as a reference and the other X-ray projections may be aligned with respect to it.

With the foregoing in mind, in one embodiment a reference pixel position 68 is selected, and the other pixel positions on the projection are resampled applying linear weighting, non-linear weighting and so forth as mentioned above to align or line up with respect to the reference pixel position. In one such implementation, a correction factor for a focal spot is calculated using the following equation:

$$E(i) = \frac{\sum_n p_1(n) - \sum_n P_i(n)}{M} \quad (1)$$

where:
E(i): is the correction factor for focal spot(i)
$p_1(n)$: is the projection value for the first focal spot in the sub-region as illustrated in FIG. 5

$P_i(n)$: is the projection value in each sub-region from focal spot i, as illustrated in FIG. 5
n: is the sampling point index in the sub-region
M: is the number of pixels in the sub-region.

Figure 6:
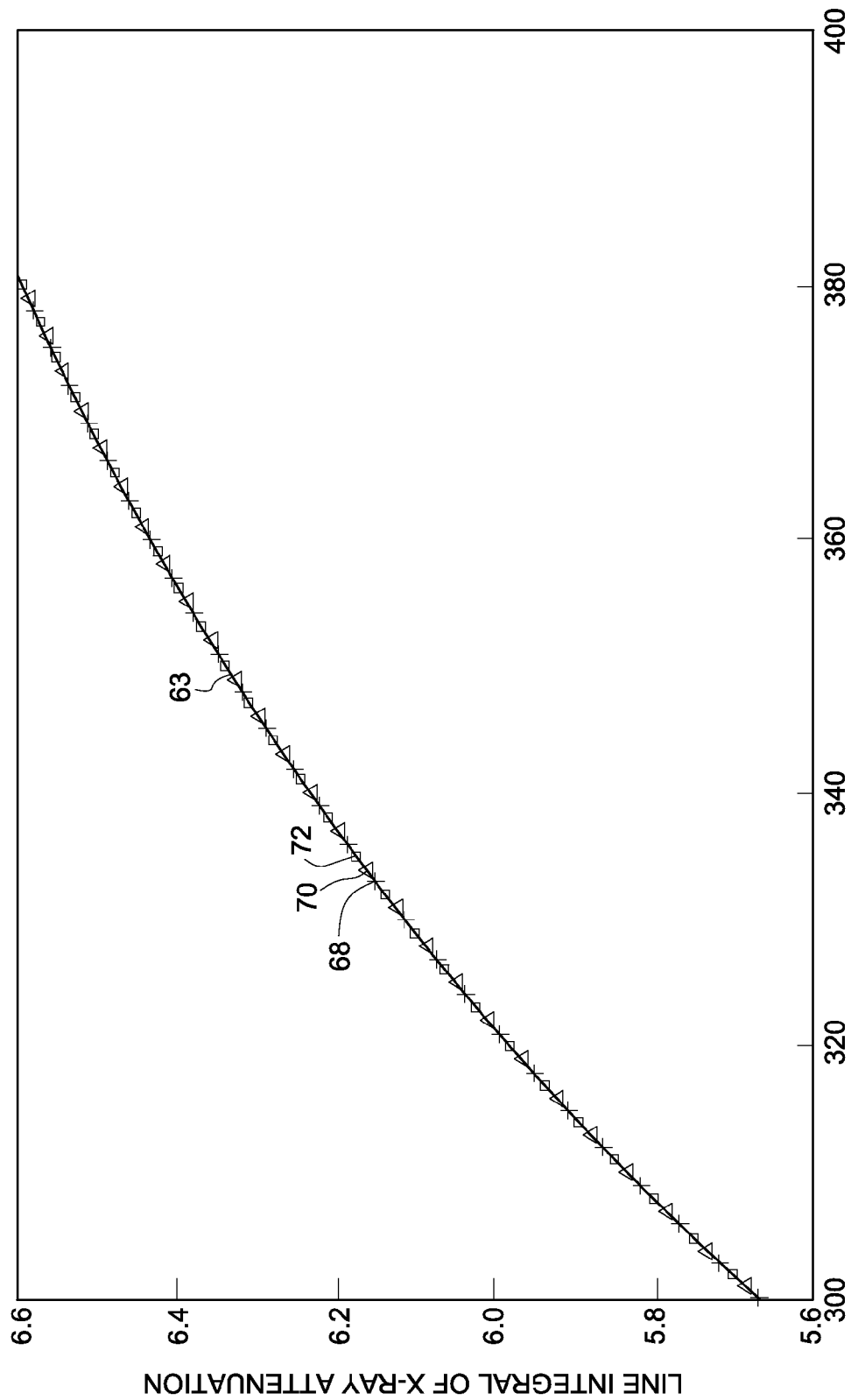
FIG. 6 depicts the sub-region of the interleaved projection profile of the image of a phantom after correction in accordance with the aspects of the present technique.

In this implementation, for all sampled projection values $p_i(n)$ as illustrated in FIG. 4, in the sub-region from focal spot i, the correction factor E(i) is added to yield the new projection values. This can be represented by the following equation:

$$p_i^{corr}(n) = p_i(n) + E(i) \quad (2)$$

where:
$p_i^{corr}(n)$: is the corrected projection values for focal spot i
This process is repeated for all the focal spot positions. Further, the process may be repeated for each sub-region. The correction removes the differential errors or DC errors in the sub-region of the projections from different focal spots. Thereafter, the projections are interleaved, as depicted in FIG. 6. In the depicted example, the X-ray projection 62 from the first focal spot position, the X-ray projection 64 from second focal spot and the X-ray projection from the third focal spot are interleaved to obtain an interleaved projection 63 having an increased sampling frequency.

A reconstruction technique may then be performed on the corrected projection values obtained by the above discussed technique. As noted above, the reconstruction technique may be one or more of a filtered backprojection, iterative filtered backprojection, iterative reconstruction, statistical reconstruction techniques, or other suitable reconstruction technique.

Figure 7:
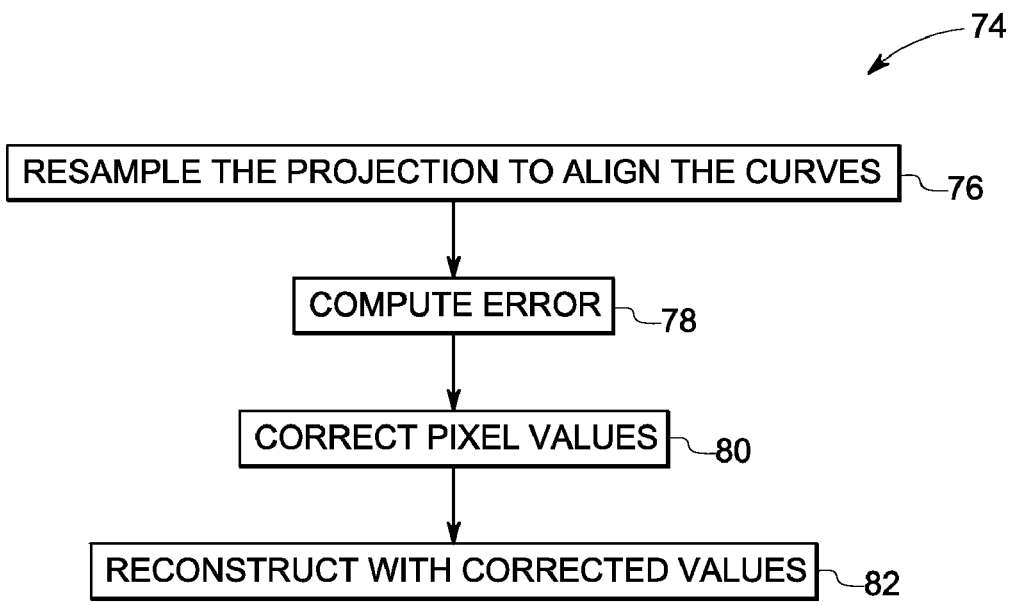
FIG. 7 is a flow chart depicting an image reconstruction process according to one embodiment of the present technique.

Referring now to FIG. 7, a control scheme 74 for performing pixel value correction and subsequent image reconstruction in accordance with aspects of the present technique is depicted via a flowchart. The control scheme 74 includes the steps of resampling a projection to align the curves at step 76, computing the error at step 78, correcting the pixel values at step 80, and reconstructing with the corrected pixel values at step 82. The computation of the error may be performed via the equation 1 discussed above.

Figure 8:
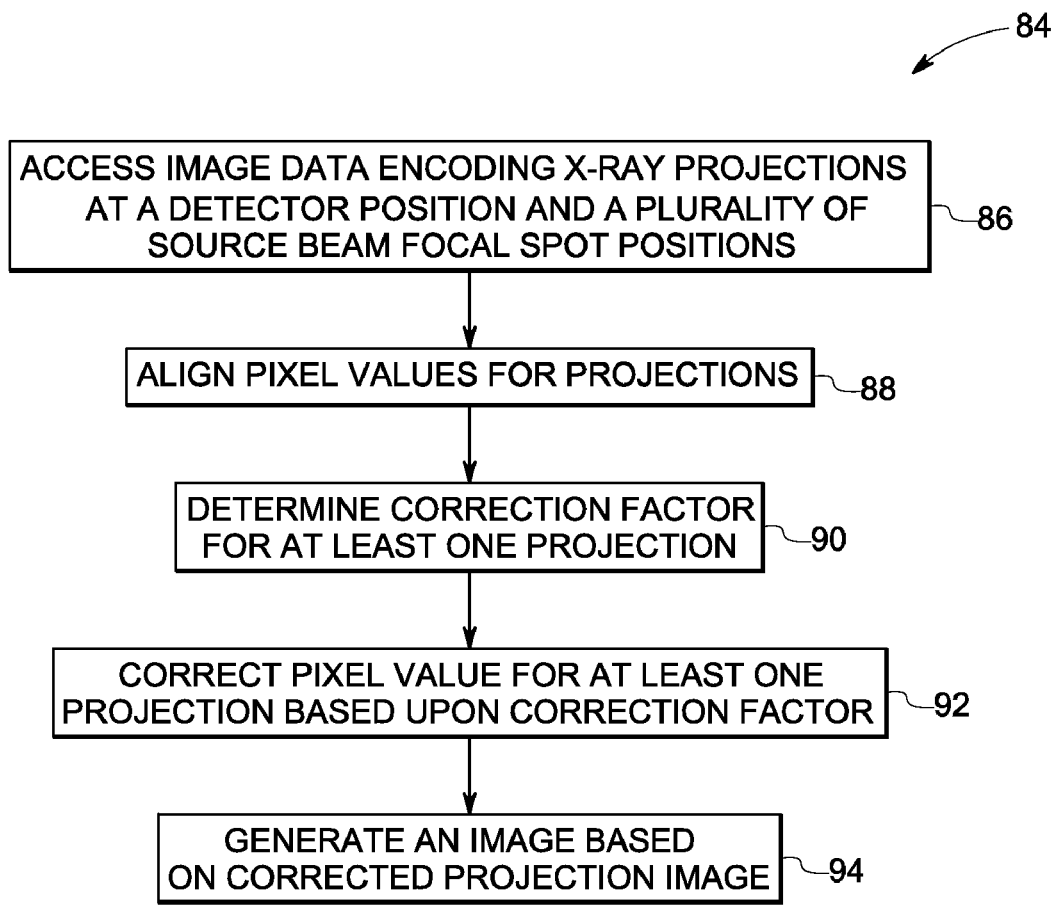
FIG. 8 is a flow chart depicting the image reconstruction process of FIG. 7 in greater detail according to one embodiment of the present technique.

By means of further example, the pixel value correction, alignment and subsequent image reconstruction technique illustrated in FIG. 6 may further be elaborated as shown in FIG. 8. As illustrated in FIG. 8, a control scheme 84 includes the steps of accessing image data encoding X-ray projections at a detector position and a plurality of source beam focal spot positions at step 86. The control scheme 84 further includes the steps of aligning pixel values for projections at step 88, determining a correction factor for at least one projection at step 90, correcting pixel values for at least one projection based upon the correction factor at step 92 and generating an image based on the corrected projection image at step 94.

The above discussed techniques of generating an image based on the corrected and aligned pixel values have many advantages, including reduction or minimization of ring artifacts in a high definition CT images. Further, the technique described in the various embodiments discussed above may also reduce image noise originated from interleaving projections acquired at different X-ray focal spots. Moreover, the techniques have little or no impact on the image resolution and may also allow high definition CT images to be devoid of focal spot imperfection induced artifacts.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for producing a computed tomography image, comprising:
   accessing image data encoding X-ray projections at a detector position and a plurality of X-ray source beam focal spot positions;
   aligning pixel values for the projections in a direction of deviation of the positions;
   determining a correction factor for at least one of the projections based upon the aligned pixel values and upon a sum of the projections; and
   correcting the pixel values for the at least one of the projections using the correction factor.

2. The method of claim 1, comprising acquiring the image data for a subject of interest.

3. The method of claim 1, comprising reconstructing an image based upon the corrected pixel values.

4. The method of claim 1, wherein the X-ray source beam focal spot positions are obtained by impacting a target within a X-ray source by an electron beam steered differently at the target for each focal spot position.

5. The method of claim 1, wherein the X-ray source beam focal spot positions are deviated in a direction of rotational movement of the detector and the X-ray source.

6. The method of claim 1, wherein the X-ray source beam focal spot positions are deviated in a direction transverse to an image plane.

7. The method of claim 1, wherein pixel values for a reference projection are used for determination of the correction factor for the at least one of the projections.

8. The method of claim 7, wherein the pixel values for the reference projection are not corrected.

9. The method of claim 1, comprising grouping the pixel values into a plurality of sub-regions, and wherein the aligning, determining and correcting steps are performed separately for each sub-region based upon pixel values for the respective projections in the respective sub-region.

10. The method of claim 1, wherein the correction factor corrects for deviation of X-ray attenuation between the projections.

11. A method for producing a computed tomography image, comprising:
   (a) accessing image data encoding X-ray projections at a detector position and a plurality of X-ray source beam focal spot positions, the source beam focal spot positions being obtained by impacting a target within the X-ray source by an electron beam steered differently at the target for each focal spot position;
   (b) aligning pixel values for the projections in a direction of deviation of the positions;
   (c) grouping the pixel values into a plurality of sub-regions;
   (d) for each sub-region, based upon the aligned pixel values, determining a respective correction factor for at least one of the projections based upon a sum of the projections and a number of pixels in the sub-region;
   (e) for each sub-region, correcting the pixel values for the at least one of the projections based upon the respective correction factor; and
   (f) repeating steps (d) and (e) for each projection to be corrected and for each sub-region.

12. The method of claim 11, wherein the correction factors are determined using a reference projection.

13. The method of claim 12, wherein no correction factors are determined for the reference projection and pixel values for the reference projection are not corrected.

14. The method of claim 11, wherein the steps are performed in the order recited.

15. A computed tomographic imaging system, comprising:
   a processor configured to access image data encoding X-ray projections at a detector position and a plurality of X-ray source beam focal spot positions; to align pixel values for the projections in a direction of deviation of the positions; to determine a correction factor for at least one of the projections based upon the aligned pixel values and upon a sum of the projections; and to correct the pixel values for the at least one of the projections based upon the correction factor.

16. The computed tomographic system of claim 15, wherein the processor is further configured to reconstruct an image based on the corrected pixel values.

17. The computed tomographic system of claim 15, further comprising: an X-ray source and a detector for acquiring of the X-ray projections.

18. The computed tomographic system of claim 15, wherein the X-ray beam focal spot positions are obtained by impacting a target within an X-ray source by an electron beam steered differently at the target for each focal spot position.

19. The computed tomographic system of claim 15, wherein the X-ray source beam focal spot positions are deviated in a direction of rotational movement of the detector and the X-ray source.

20. The computed tomographic system of claim 15, wherein the X-ray beam focal spot positions are deviated in a direction transverse to an image plane.

21. The computed tomographic system of claim 15, wherein pixel values for a reference projection are used for determination of the correction factor for the at least one of the projections.

22. The computed tomographic system of claim 21, wherein the pixel values for the reference projection are not corrected.

23. A non-transitory computer readable medium embedded with routines, which when implemented by a processor, causes a processor to implement the steps of:
   accessing image data encoding X-ray projections at a detector position and a plurality of X-ray source beam focal spot positions;
   aligning pixel values for the projections in a direction of deviation of the positions;
   determining a correction factor for at least one of the projections based upon the aligned pixel values and based upon a sum of the projections; and
   correcting pixel values for the at least one of the projections based upon the correction factor.

* * * * *